United States Patent [19]
Griffis

[11] Patent Number: 4,804,391
[45] Date of Patent: Feb. 14, 1989

[54] MEANS FOR SAMPLING THE EXHAUST AIR OF AN AIR FILTRATION UNIT

[76] Inventor: Steven C. Griffis, 2929 Avenue D, Council Bluffs, Iowa 51501

[21] Appl. No.: 179,864

[22] Filed: Apr. 11, 1988

[51] Int. Cl.⁴ ............................................. B01D 35/02
[52] U.S. Cl. ...................................... 55/270; 55/500; 73/863.23; 73/864.34
[58] Field of Search ..................... 55/270, 484, 500; 73/863.23, 863.83, 864.34

[56] References Cited

U.S. PATENT DOCUMENTS

| | | | |
|---|---|---|---|
| 3,903,745 | 9/1975 | Bolser | 73/864.34 X |
| 3,965,748 | 6/1976 | Boubel et al. | 73/863.23 X |
| 4,721,517 | 1/1988 | Cloutier | 55/270 |
| 4,736,637 | 4/1988 | Stock | 73/863.83 |

Primary Examiner—Charles Hart
Attorney, Agent, or Firm—Zarley, McKee, Thomte, Voorhees & Sease

[57] ABSTRACT

A plurality of air filtration units located within an enclosed contaminated space have their exhaust connected to an air box located within the enclosed space. The interior of the air box is in communication with an area outside of the enclosed contaminated space. An isolation chamber is mounted on one wall of the air box to permit the insertion of air sampling cassettes into the interior of the air box so that the exhaust air in the air box may be monitored. The isolation chamber also permits the selective removal of the air sampling cassettes from the air box. In both the insertion and removal operations, the isolation chamber prevents contaminants from being released into the enclosed space.

11 Claims, 4 Drawing Sheets

MEANS FOR SAMPLING THE EXHAUST AIR OF AN AIR FILTRATION UNIT

BACKGROUND OF THE INVENTION

This invention relates to a means for sampling the exhaust air of an air filtration unit and more particularly to means for the exhaust air of an air filtration unit which is being used in an asbestos abatement action.

Airborne asbestos contamination in buildings is a significant environmental problem. Various diseases have been linked with industrial exposure to airborne asbestos, and the extensive use of asbestos products in buildings has raised concerns about exposure to asbestos in nonindustrial settings. Surveys conducted by the Environmental Protection Agency (EPA) estimate that asbestos-containing materials can be found in approximately 31,000 schools and 733,000 other public and commercial buildings in this country.

In an effort to avoid the hazards associated with exposure to airborne asbestos, abatement actions or procedures are being extensively conducted and the Environmental Protection Agency has published a booklet entitled "Guidance for Controlling Asbestos-Containing Materials in Buildings". During the abatement action, one or more air filtration units, usually several air filtration units, are positioned throughout the work site to filter the air in the work area.

During the abatement action, it is recommended that the exhaust air of the air filtration units be monitored. Inasmuch as the exhaust of the air filtration units are normally exhausted to the atmosphere, the monitoring or sampling of the exhaust air is quite difficult. For example, if the abatement action is being conducted on the 14th floor of a high-rise building, it is extremely difficult to sample the exhaust air as the air is discharged from the 14th floor.

When a plurality of air filtration units are being used within the enclosed work site, and the exhaust of the same are being exhausted to the atmosphere outwardly of the building, the contamination problem is encountered when a particular air filtration unit is taken out of service for maintenance. For example, if an air filtration unit is shut down, back pressure on the exhaust side thereof can cause asbestos fibers to be discharged from the contaminated side of the HEPA filter into the work site when the air filtration unit is shut down.

Further, when a plurality of air filtration units have been used during the abatement action, a large number of the air filtration units must be shut down just prior to the final air sampling within the work site. When the air filtration unit is shut down, back pressure on the exhaust side of the air filtration unit can also cause the discharge of asbestos fibers into the work site, as previously described.

Therefore, it is a principal object of the invention to provide a means for sampling the exhaust air of an air filtration unit.

A further object of the invention is to provide a means for sampling the exhaust air of an air filtration unit and more particularly a means for sampling the exhaust air of an air filtration unit which is being used in an asbestos abatement action.

Yet another object of the invention is to provide a means for sampling the exhaust air of an air filtration unit to permit the convenient sampling of the same.

Still another object of the invention is to provide a means whereby the exhaust of air filtration units may be selectively closed by means of dampers to prevent back pressure being subjected to the air filtration unit which could dislodge fibers from the HEPA filter and re-contaminate the work site.

Still another object of the invention is to provide a means for sampling the exhaust air of an air filtration unit including means for changing the air sampler cassettes without contaminating them or the exhaust air.

These and other objects will be apparent to those skilled in the art.

SUMMARY OF THE INVENTION

Figure 1:
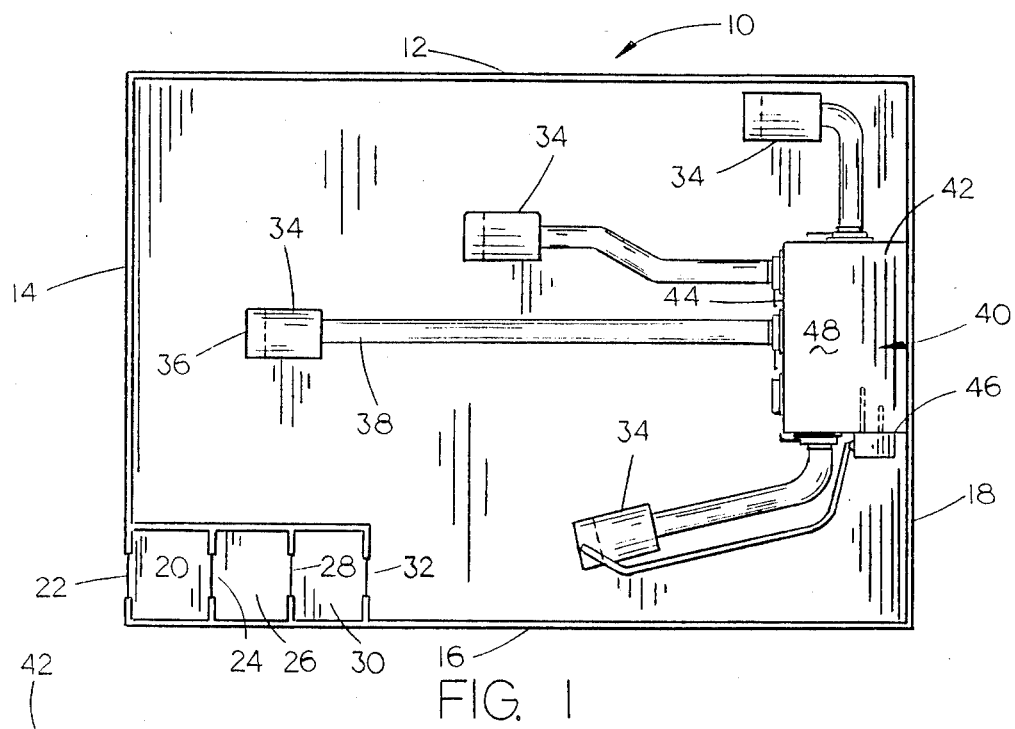
FIG. 1 is a schematic view illustrating the apparatus of this invention being used to sample the exhaust air being discharged from an enclosed contaminated area.
Figure 2:
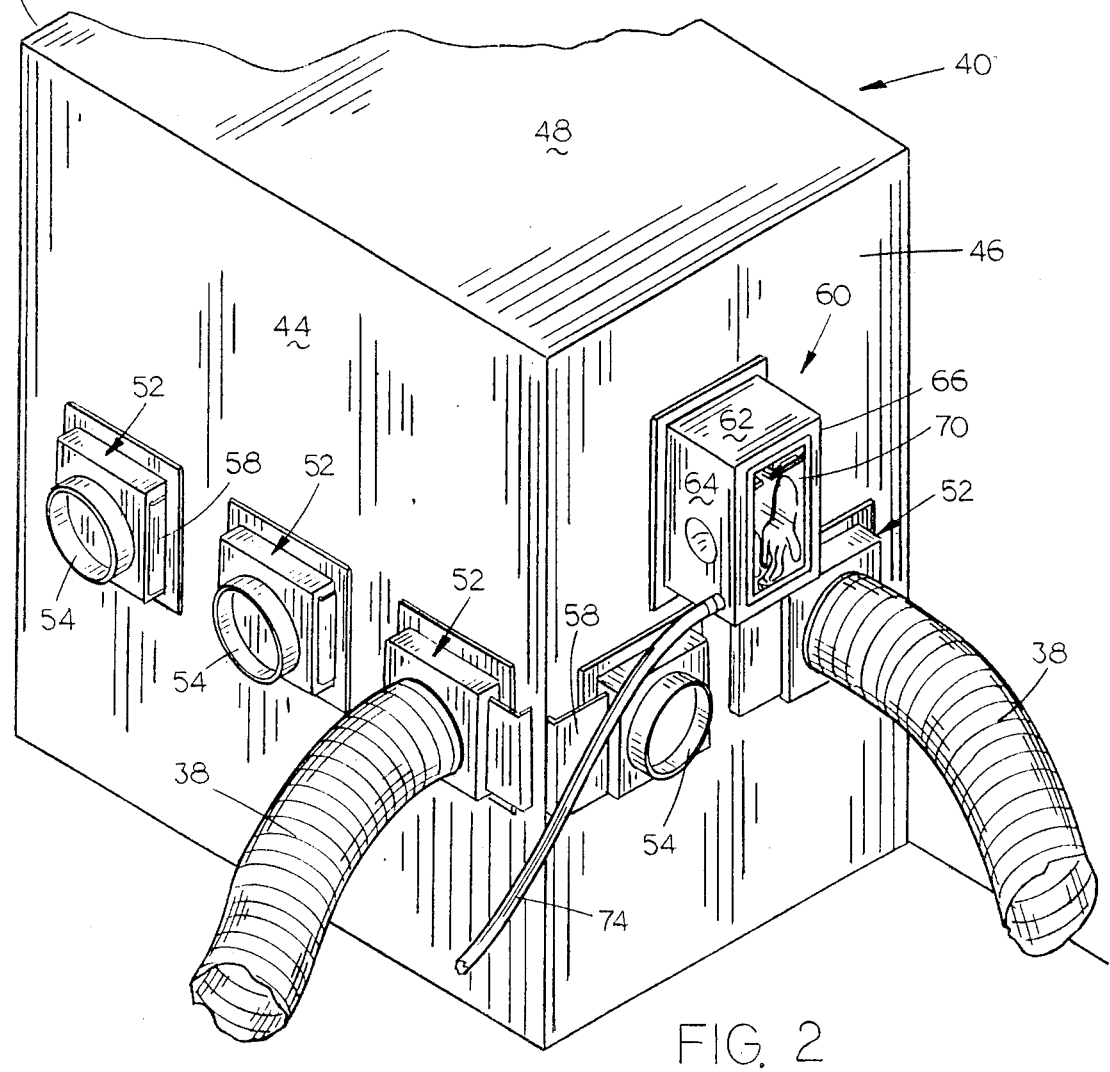
FIG. 2 is a partial perspective view illustrating the apparatus of this invention mounted on an air box into which the exhaust of the air filtration units are discharged.
Figure 3:
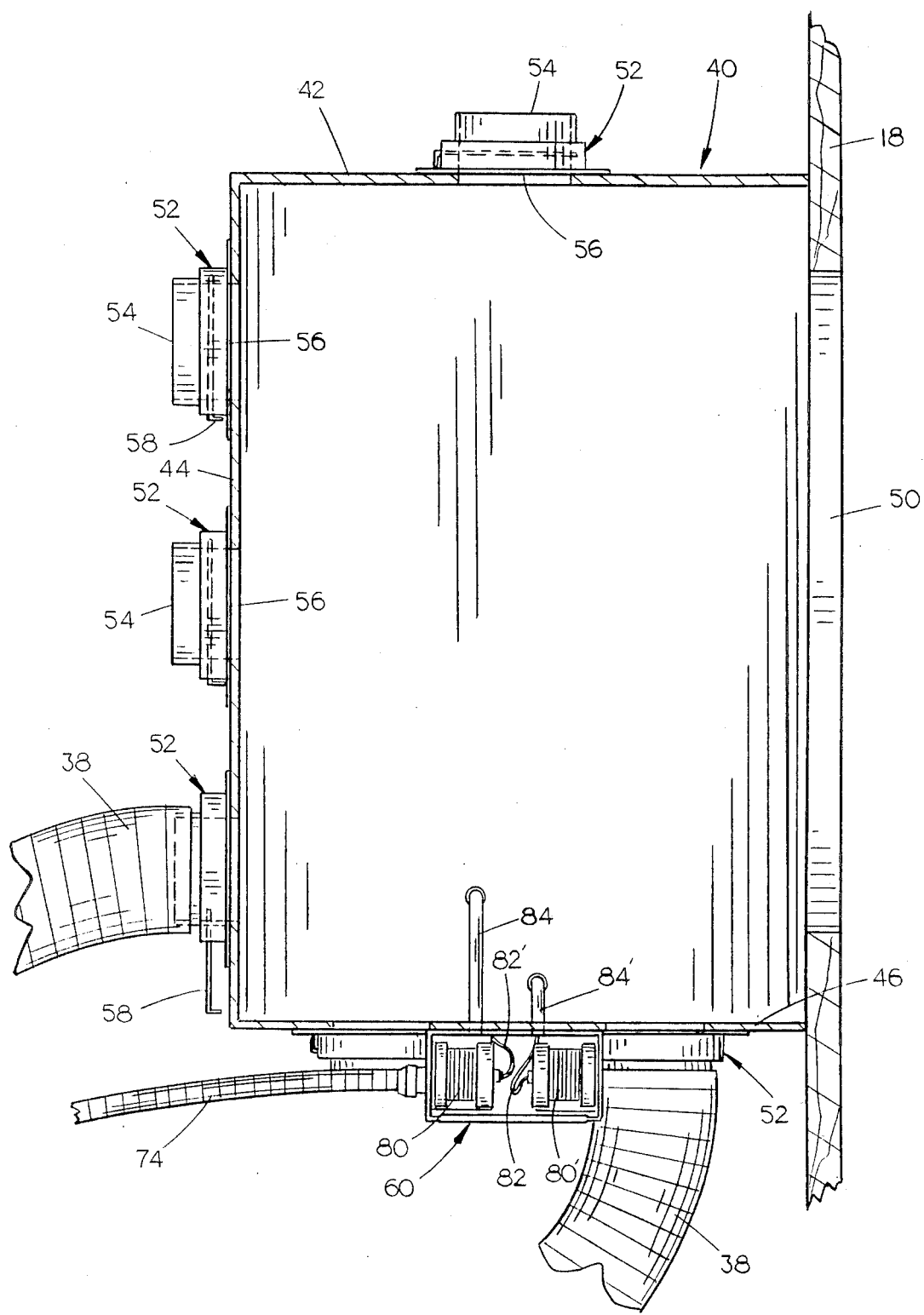
FIG. 3 is a top view of FIG. 2 with portions thereof cut away to more fully illustrate the invention.
Figure 5:
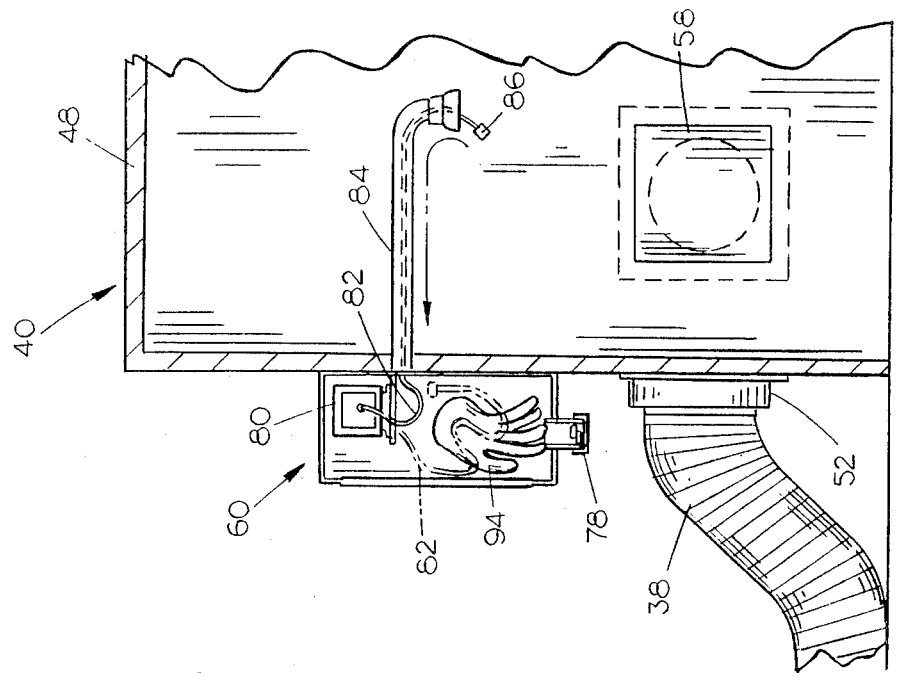
FIG. 5 is a sectional view illustrating the apparatus of this invention mounted on the air box.
Figure 4:
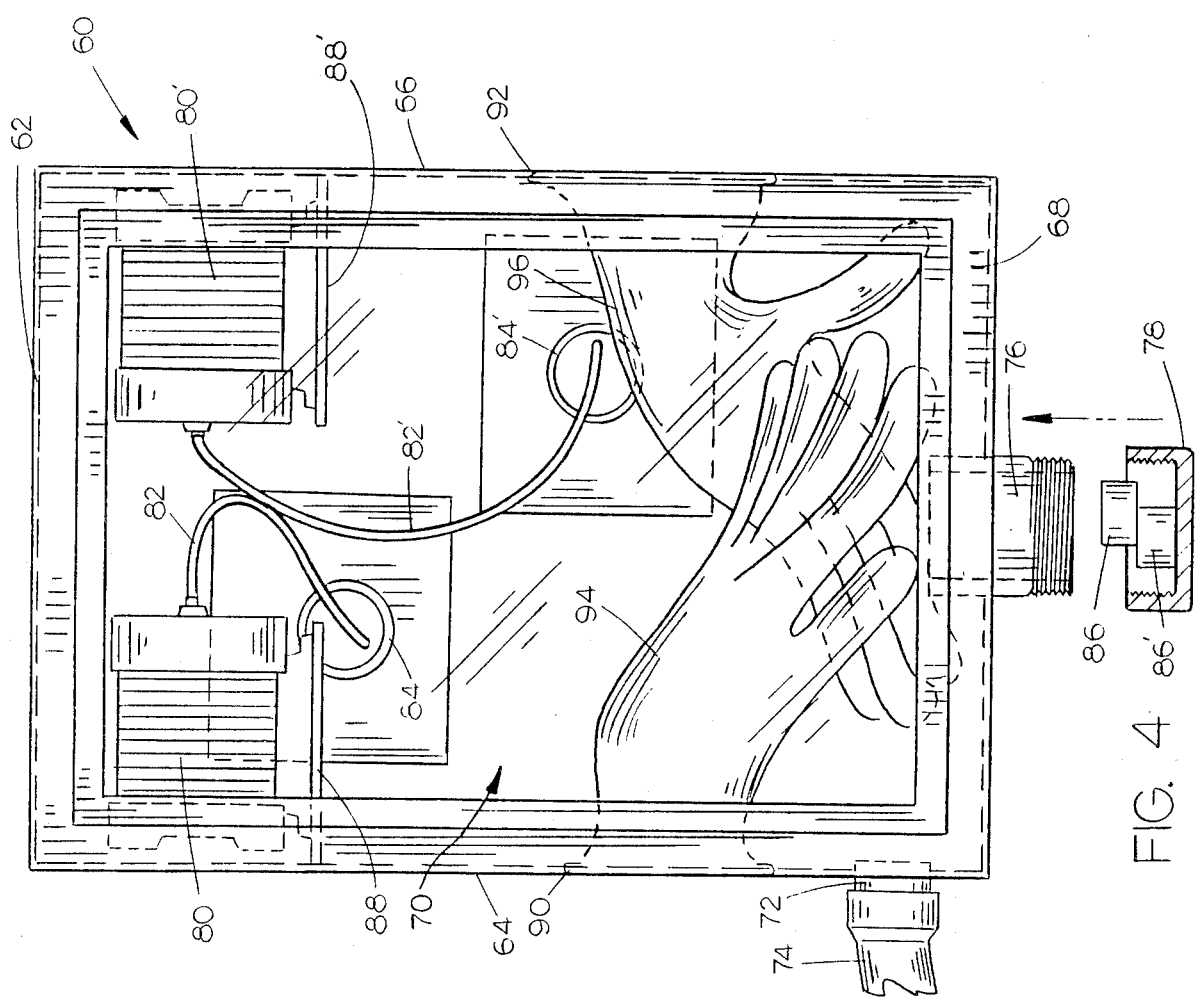
FIG. 4 is a front elevational view of the apparatus of this invention.

An apparatus is disclosed for monitoring the exhaust air of the exhausts of a plurality of air filtration units which are located within an enclosed space wherein an asbestos abatement procedure or action is taking place. An air box means is created and is positioned adjacent one wall of the enclosed space with the air box having a discharge in communication with an area outside of the work site. Each of the air filtration units employed within the work site has an exhaust conduit extending therefrom which is in communication with the air box means. A damper is imposed between the exhaust conduit of each of the air filtration units and the air box. An isolation chamber or compartment is mounted on one of the walls of the air box means and has one or more air pumps positioned therein. Each of the air pumps in the isolation chamber has a flexible hose extending from the intake thereof into the air box means. A conventional air sampler cassette is mounted on the end of each of the hoses within the air box means. A flexible conduit extends from the isolation chamber to the intake side of one of the air filtration units so that the air filtration unit will tend to draw air from the interior of the isolation chamber to the intake side of the air filtration unit. The isolation chamber is also provided with a selectively closable access port at the lower end thereof. A pair of isolation gloves are mounted on the sides of the isolation chamber to permit an to insert his hands thereinto to work within the interior of the isolation chamber. When is it desired to remove the air samplers from the hoses, the operator inserts his hands into the gloves and pulls the hoses into the interior of the isolation chamber and then removes the air samplers from the ends of the hose. If desired, and is usually the case, new air samplers are then connected to the ends of the hoses with the hoses then being fed into the air box means. The contaminated air sampler are capped and removed from the interior of the isolation chamber through the selectively closable access port. Any air that enters the interior of the isolation chamber through the access port during the time that the access port is open will be drawn directly into the inlet of the air filtration unit connected to the isolation chamber.

A modified form of the invention is disclosed wherein the isolation chamber is mounted on the exhaust conduit extending from an air filtration unit.

DESCRIPTION OF THE PREFERRED EMBODIMENT

The numeral 10 refers generally to an enclosed space or work site in which asbestos is being removed from or in which other asbestos abatement actions or procedures are being conducted. Enclosed space 10 is either defined by the walls of the building structure or by temporary walls. In either case, the walls are referred to generally by the reference numeral 12, 14, 16 and 18. The walls would normally be sealed with a plastic sheeting material to prevent the escape of fibers therefrom. In most projects, a clean room 20 is provided having an entrance 22.

Door 24 connects clean room 20 with shower room 26. Door 28 connects shower room 26 with equipment room 30. Door 32 connects equipment room 30 with enclosed space 10. Doors 24, 28 and 32 are normally comprised of a flexible plastic material which may be pushed aside when passing therethrough.

During the asbestos abatement action, a plurality of air filtration units 34 are located throughout the enclosed space 10. Each of the air filtration units 34 has an inlet end 36 and a flexible conduit 38 extending from exhaust side thereof. Theretofore, the exhaust conduits 38 would normally be placed in communication with a window, door, etc. moving outwardly into another area or into the atmosphere. In most abatement actions, it is necessary to monitor the exhaust air passing through the exhaust conduits 38 and the same is extremely difficult if the exhaust air is being discharged into the atmosphere.

To overcome the shortcomings of the conventional practice, an air box means 40 is provided within the work site or enclosed space 10. Air box means 40 includes walls 42, 44 and 46. The upper ends of the walls 42, 44, and 46 are closed by a top wall 48. In some cases, the air box means 40 will also include a bottom wall. Walls 42 and 46 are sealed to the wall 18 by sealing tape, plastic or the like. The interior of air box means 40 is in communication with the air exhaust passageway 50 provided in wall 18.

A plurality of dampers 52 are mounted on the exterior surfaces of walls 42, 44 and 46 and have inlet ends 54 which are in communication with the conduits 38. Each of the dampers 52 has a discharge opening 56 which is in communication with the interior with air box means 40. A selectively slidable damper plate 58 is mounted on each of the dampers 52 to permit communication between inlet and discharge openings 54 and 56 or to prevent air communication therebetween.

The numeral 60 refers to an isolation chamber which is mounted on any of the walls 42, 44 or 46 but which is shown to be mounted on wall 46 in the drawings. Isolation chamber 60 includes a top wall 62, opposite side walls 64 and 66, bottom wall 68, and transparent front wall 70. Side wall 64 is provided with a discharge port 72 which is in communication with a hose 74 which extends to the inlet side of one of the air filtration units 34.

Bottom wall 68 is provided with pipe stub 76 which is in communication with the interior of isolation chamber 60 and which extends downwardly therefrom. The lower end of pipe stub 76 is externally threaded and is adapted to receive a cap 78.

A pair of air pumps 80 and 80' are mounted within the interior of isolation chamber 60 as illustrated in the drawings. Although a pair of the air pumps 80 and 80' are illustrated, a single air pump could be utilized if so desired, although it is preferred that at least a pair of the air pumps be utilized.

Air pump 80 is of conventional design and has an air hose 82 extending from the inlet side thereof through a conduit 84 which extends from the interior of isolation chamber 60 into the interior of air box means 40. A conventional air sampler 86 is mounted on the end of air hose 82 and is positioned within the interior of air box 40 to sample the air therein in conventional fashion. The discharge side of air pump 80 is exhausted to the interior of isolation chamber 60. As seen in the drawings, air pump 80 is mounted on a bracket or shelf 88. Similarly, air pump 80' has an air hose 82' extending from the inlet side thereof through a conduit 84' which extends into the interior of air box means 40. A conventional air sampler cassette 86' is mounted on the end of hose 82'. The exhaust side of pump 80' is in communication with the interior of isoaation chamber 60. Air pump 80' is mounted on shelf or bracket 88'.

A pair of access openings 90 and 92 are provided in side walls 64 and 66 and have the peripheries of gloves 94 and 96 therein to permit the operator to insert his hands into the interiors of the gloves 94 and 96 so as to be able to service the components within the interior of isolation chamber 60.

In operation, assuming that the air samplers 86 and 86' are mounted on the hoses 82 and 82' within air box means 40, the manner of removing the air sampler cassettes 86 and 86' from the air box means 40 is as follows. Pump 80 is deactivated and the operator inserts his hands into the gloves 94 and 96. The operator then grasps the air hose 82 and pulls the air hose into the interior of the isolation chamber 60 so that the air sampler cassette 86 may be removed from the end of the air hose. The air sampler cassette 86 is then capped and removed from the air hose 82 and then placed into the interior of pipe stub 76. The same procedure is then followed with respect to the air sampler cassette 86'.

The operator then removes his hands from the interiors of the gloves 94 and 96 and unscrews cap 78 from pipe stub 76. When the cap 78 has been removed from the pipe stub 76, the operator may collect the air sampler cassettes 86 and 86'. New air sampler cassettes may then be placed into the interior of the cap 78 and the cap 78 is then screwed onto the threaded end of the pipe stub 76. The operator then inserts his hands into the gloves 94 and 96 and removes the air sampler cassettes from the interior of the pipe 76, uncaps and screws the same onto the ends of the air hoses 82 and 82'. The air hoses are then passed outwardly through their respective conduits 84 and 84' so that they once again in communication with the interior of the air box means.

When cap 78 is removed as previously described, any asbestos fibers being drawn upwardly thereinto from the work site or enclosed space 10 will be drawn into the conduit 74 due to the suction applied thereto. Thus, contaminated air entering the pipe stub 76 will not contaminate any of the other components within the isolation chamber 60 since the air will pass substantially directly into the conduit 74.

When it is desired to service an individual air filtration unit, the associated damper 52 is closed prior to the air filtration unit being shut down. The closing of the associated damper prevents any back air flow through the air filtration unit from the air box means 40. If such a damper was not provided, objectional back pressure on the air filtration unit could cause contaminants therein to be discharged back into the work site or enclosed space 10. The dampers 50 also permit the system to be shut down gradually to maintain the negative air pressure therein in a reduced rate just prior to final air sampling.

The dampers 50 also make the initial hookup easier, e.g. if they are installed in a wall instead of air box, you can cut any shape hole and then place the damper and seal as opposed to cutting an accurate round hole corresponding to the diameter of the exhaust hose and then trying to seal the same.

Figure 6:
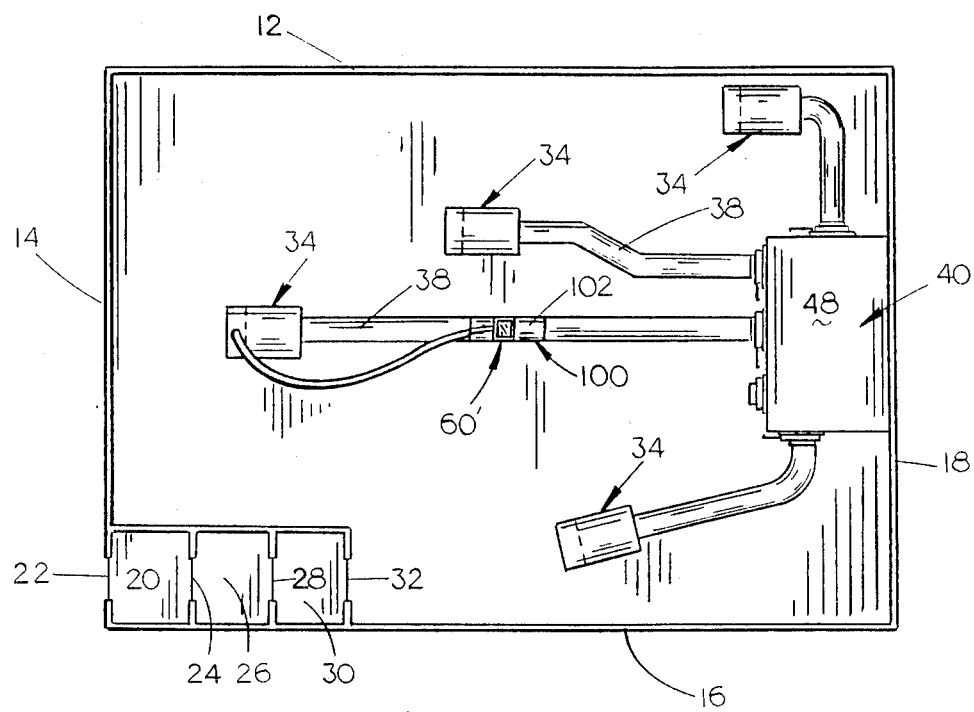
FIG. 6 is a schematic view similar to FIG. 1 except that the apparatus of this invention is mounted on the exhaust conduit of an air filtration unit.
Figure 7:
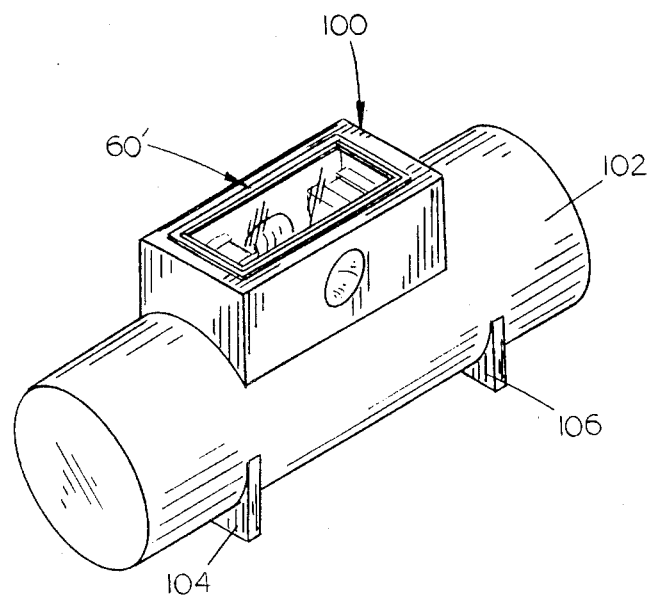
FIG. 7 is a perspective view of the in-line sample unit of FIG. 6.

A modified form of the system is illustrated in FIGS. 6 and 7. In some cases, it may be desirable to be able to test the exhaust air being discharged from a particular air filtration unit 34. To permit such a testing, an in-line apparatus is provided which is referred to generally by the reference numeral 100 in FIGS. 6 and 7. The isolation chamber 60' illustrated in FIGS. 6 and 7 is substantially identical to the isolation chamber 60 except that isolation chamber 60' is mounted upon a tubular member 102 supported by legs 104 and 106. Conduit 38 is split with the ends of the conduit 38 being mounted on and sealed to the ends of the tubular member 102. The air sampling cassettes of the isolation chamber 60' are extended downwardly into the interior of the tubular member 102 so that the air sampling cassettes may sample the exhaust air passing through conduit 38 and the tubular member 102. Although FIG. 6 illustrates a hose connecting the unit 100 with the air inlet of unit 34, such is not normally required since the interior of conduit 102 is always under positive pressure.

In another embodiment, the isolation chamber 60 could be mounted directly on the inside surface of wall 18 with the air sampling cassettes 86 and 86' passing outwardly through the wall for positioning in the exhaust air being discharged through an exhaust opening in the wall.

Thus it can be seen that the invention accomplishes at least all of its stated objectives.

I claim:

1. In combination,
   an enclosed space in which an asbestos abatement action is being conducted,
   at least one air filtration unit in said enclosed space and having an air intake and an air exhaust,
   said air intake of said air filtration unit being in operative communication with said enclosed space,
   a first air conduit having intake and discharge ends,
   said intake end of said first air conduit being in operative communication with said air exhaust of said air filtration unit,
   said discharge end of said first air conduit being in operative communication with an area outside of said enclosed space,
   an air sampling means in operative communication with the exhaust air of said air filtration unit,
   an isolation chamber means positioned remotely of said air sampling means,
   a second air conduit means having an intake end in communication with the interior of said isolation chamber and a discharge end in communication with the air intake of said air filtration unit whereby said air filtration unit will draw air from the interior of said isolation chamber into said second air conduit and thence into said air filtration unit,
   an electrically operated air pump means positioned in said isolation chamber and having an intake end and a discharge end,
   an air hose means extending from said intake end of said air pump means to said air sampling means whereby a portion of said exhaust air will be drawn into said air sampling means,
   a pair of gloves mounted on said isolation chamber in a sealed fashion and extending thereinto with the interiors of said gloves being accessible from the exterior of said isolation chamber whereby an operator may insert his hands into the gloves so that the operator may grasp said air hose means to pull said hose means and said air sampling means into said isolation chamber to permit the removal of said air sampling means from said air hose means,
   and a selectively closable access port provided on said isolation chamber for permitting the removal of said air sampling means from the interior of said isolation chamber after said air sampling means has been removed from said air hose means.

2. The combination of claim 1, wherein said intake end of said second air conduit means and said access port are located closely adjacent one another so that air drawn into the interior of said isolation chamber, through said access port, when said access port is open will tend to be drawn substantially directly into said intake end of said second air conduit.

3. The combination of claim 1 wherein a passageway means is provided between said isolation chamber and the location of said air sampling means, said air hose means selectively slidably extending through said passageway means.

4. The combination of claim 3 wherein said passageway means comprises a hollow pipe.

5. The combination of claim 1, wherein an air box means is provided in said enclosed space and has the interior thereof in communication with an area outside of said enclosed space, said discharge end of said first conduit being in operative communication with the interior of said air box means.

6. The combination of claim 5, wherein said isolation chamber is mounted on said air box means and said air hose means extends into said air box means.

7. The combination of claim 5, wherein a selectively closable damper means is provided between the discharge end of said first conduit and said air box means.

8. The combination of claim 1, wherein said isolation chamber is operatively mounted on said first conduit and said air sampling means is removably positioned in said first conduit.

9. In combination,
   an enclosed space in which an asbestos abatement action is being conducted,
   at least one air filtration unit in said enclosed space and having an air intake and an air exhaust,
   said air intake of said air filtration unit being in operative communication with said enclosed space, a first air conduit having intake and discharge ends,
said intake end of said first air conduit being in operative communication with said air exhaust of said air filtration unit,
said discharge end of said first air conduit being in operative communication with an area outside of said enclosed space,
a tubular member imposed in air first air conduit,
an air sampling means removably positioned in said tubular member,
an isolation chamber positioned on said tubular member,
an electrically operated air pump means positioned in said isolation chamber and having an intake end and a discharge end,
an air hose means extending from said intake end of said air pump means to said air sampling means whereby a portion of said exhaust air will be drawn into said air sampling means,
a pair of gloves mounted on said isolation chamber in a sealed fashion and extending thereinto with the interiors of said gloves being accessible from the exterior of said isolation chamber whereby an operator may insert his hands into the gloves so that the operator may grasp said air hose means to pull said hose means and said air sampling means into said isolation chamber to permit the removal of said air sampling means from said air hose means,
and a selectively closable access port provided on said isolation chamber for permitting the removal of said air sampling means from the interior of said isolation chamber after said air sampling means has been removed from said air hose means.

10. An apparatus for sampling the exhaust air of an air filtration unit which is being used in an enclosed space in which an asbestos abatement action is being conducted said air filtration unit having an air intake and an air exhaust, said air intake of said air filtration unit being in operative communication with said enclosed space, comprising,
a first air conduit having intake and discharge ends,
said intake end of said first air conduit being in operative communication with said air exhaust of said air filtration unit,
said discharge end of said first air conduit being in operative communication with an area outside of said enclosed space,
an air sampling means in operative communication with the exhaust air of said air filtration unit,
an isolation chamber means positioned remotely of said air sampling means,
a second air conduit means having an intake end in communication with the interior of said isolation chamber and a discharge end in communication with the air intake of said air filtration unit whereby said air filtration unit will draw air from the interior of said isolation chamber into said second air conduit and thence into said air filtration unit,
an electrically operated air pump means positioned in said isolation chamber and having an intake end and a discharge end,
an air hose means extending from said intake end of said air pump means to said air sampling means whereby a portion of said exhaust air will be drawn into said air sampling means,
a pair of gloves mounted on said isolation chamber in a sealed fashion and extending thereinto with the interiors of said gloves being accessible from the exterior of said isolation chamber whereby an operator may insert his hands into the gloves so that the operator may grasp said air hose means to pull said hose means and said air sampling means into said isolation chamber to permit the removal of said air sampling means from said air hose means,
and a selectively closable access port provided on said isolation chamber for permitting the removal of said air sampling means from the interior of said isolation chamber after said air sampling means has been removed from said air hose means.

11. In combination,
an enclosed space in which an asbestos abatement action is being conducted,
at least one air filtration unit in said enclosed space and having an air intake and an air exhaust,
said air intake of said air filtration unit being in operative communication with said enclosed space,
a first air conduit having intake and discharge ends,
said intake end of said first air conduit being in operative communication with said air exhaust of said air filtration unit,
a tubular member operatively connected to said first air conduit,
an air sampling means removably positioned in said tubular member,
an isolation chamber positioned on said tubular member,
an electrically operated air pump means positioned in said isolation chamber and having an intake end and a discharge end,
an air hose means extending from said intake end of said air pump means to said air sampling means whereby a portion of said exhaust air will be drawn into said air sampling means,
a pair of gloves mounted on said isolation chamber in a sealed fashion and extending thereinto with the interiors of said gloves being accessible from the exterior of said isolation chamber whereby an operator may insert his hands into the gloves so that the operator may grasp said air hose means to pull said hose means and said air sampling means into said isolation chamber to permit the removal of said air sampling means from said air hose means,
and a selectively closable access port provided on said isolation chamber for permitting the removal of said air sampling means from the interior of said isolation chamber after said air sampling means has been removed from said air hose means.

* * * * *